United States Patent [19]

Rodriguez et al.

[11] 4,162,325
[45] Jul. 24, 1979

[54] N-SUBSTITUTED LACTAMS

[75] Inventors: Ludovic Rodriguez, Brussels; Lucien Marchal, Lillois, both of Belgium

[73] Assignee: UCB, Société Anonyme, Saint-Gilles-lez-Brussels, Belgium

[21] Appl. No.: 843,692

[22] Filed: Oct. 19, 1977

[30] Foreign Application Priority Data

Oct. 22, 1976 [GB] United Kingdom .............. 43934/76

[51] Int. Cl.$^2$ .................... C07D 207/26; A61K 31/40
[52] U.S. Cl. .................................... 424/274; 546/221; 546/243; 260/326.4; 260/326.43; 424/244; 424/267
[58] Field of Search ........................ 260/326.43, 326.4; 424/274

[56] References Cited

U.S. PATENT DOCUMENTS

| | | | |
|---|---|---|---|
| 3,121,723 | 2/1964 | Korchner | 260/326.43 |
| 3,459,738 | 8/1969 | Morren | 260/326.45 |

FOREIGN PATENT DOCUMENTS 2507576  9/1975  Fed. Rep. of Germany ...... 260/326.43

OTHER PUBLICATIONS

Djokic et al.; Chem. Abs., vol. 87:135051j (1977), Abstract of Ger. Offen. 2,701,450.
Merck Index; 9$^{th}$; #7282.

*Primary Examiner*—Donald G. Daus
*Assistant Examiner*—Mary C. Lee
*Attorney, Agent, or Firm*—Wenderoth, Lind & Ponack

[57] ABSTRACT

New physiologically active N-substituted lactams having the formula

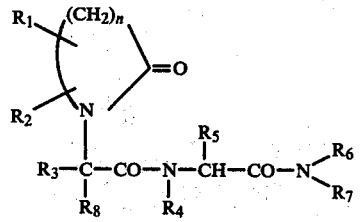

wherein $R_1$, $R_2$, $R_3$, $R_4$, $R_5$, $R_6$ and $R_7$, represent independently a hydrogen atom, an alkyl radical containing 1 to 4 carbon atoms or a phenyl group, $R_8$ is a hydrogen atom or $R_8$ and $R_3$ together form the ethylene or trimethylene radical, and n is 3, 4 or 5, processes for the preparation thereof and pharmaceutical compositions containing the same.

12 Claims, No Drawings

N-SUBSTITUTED LACTAMS

The present invention relates to new N-substituted lactams, to the preparation thereof, to pharmaceutical compositions containing them and also to their therapeutic use.

These new compounds have the following general formula:

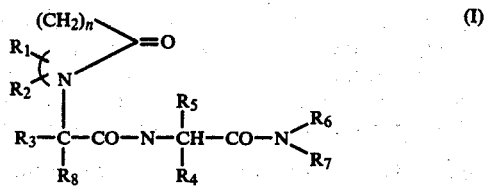

wherein
$R_1$, $R_2$, $R_3$, $R_4$, $R_5$, $R_6$ and $R_7$, represent independently a hydrogen atom, an alkyl radical containing 1 to 4 carbon atoms or a phenyl group,
$R_8$ is a hydrogen atom or $R_8$ and $R_3$ together form the ethylene or trimethylene radical, and
n is 3, 4 or 5.

Since n is 3, 4 or 5, the compounds of general formula (I) are, respectively, derivatives of 2-pyrrolidinone, 2-piperidinone or hexahydro-2H-azepine-2-one.

Preferred compounds are those of general formula (I), wherein at least one of the symbols $R_1$, $R_2$, $R_3$, $R_4$, $R_6$ and $R_7$ represents an alkyl radical containing 1 to 4 carbon atoms.

The compounds of general formula (I) have valuable pharmaceutical properties. In particular, they have a beneficial activity on mnemic processes and a protective activity against aggressions of the hypoxic type. Therefore, their first use is in the field of geropsychiatry, in which disorders of the memory occur due not only to senile cellular alterations but also to a decrease in the supply of oxygen to the brain as the result of isolated or repeated vascular accidents (see, for example, V. C. HACHINSKI, Lancet, II, (1974),207). Furthermore, the compounds of general formula (I) are useful in numerous other clinical fields, such as the prevention and treatment of cerebrovvascular or cardiovascular injuries, post-traumatic or toxic comas, memory disorders, difficulties in connection with mental concentration and the like. Compounds are already known which possess the same properties, particularly piracetam (2-oxo-1-pyrrolidineacetamide). However, this compound has the disadvantage of being effective only in large doses. Therefore, one object of the present invention is to provide compounds having the same properties as piracetam but which are effective in smaller doses.

In addition, these compounds have an interesting activity as platelet anti-aggregants and can, therefore, also be used in the treatment of myocardial infarcts resulting from platelet hyperaggregability or hyperadhesivity, in extracorporal circulations, in the case of valvular prostheses or in the treatment of thromboembolic diseases and hyperaggregability in coronary patients.

The compounds of general formula (I) can be prepared in accordance with the equation given hereinafter, which only entails known reactions. As a general rule, a lactam-N-acetic acid of formula (II) is condensed in an inert medium, such as chloroform or methylene chloride, with an amino-acid ester of formula (V) in the presence of a coupling agent, for example dicyclohexylcarbodiimide (DCC), the ester of formula (III) thus obtained then being reacted with a nitrogen compound of formula $HNR_6R_7$ for several hours at a temperature which is generally between ambient temperature and the reflux temperature, optionally in the presence of a catalyst such as sodium methoxide, thus finally giving compounds of general formula (I):

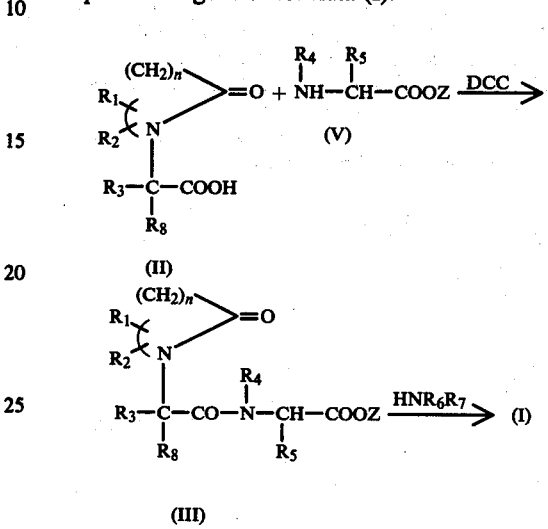

In the above equation, $R_1$ to $R_8$ and n have the same meanings as above and Z is an alkyl radical containing 1 to 4 carbon atoms or a benzyl radical.

Certain modifications of the reaction conditions may be found necessary in certain cases, for the sake of greater ease of carrying out. Thus, when the amine $HNR_6R_7$ is methylamine, the reaction is carried out at a low temperature ($-20°$ C.) because of the volatility thereof, thus making it unnecessary to work in an autoclave. Such modifications are within the scope of the expert.

As an alternative, an ester of formula (III) may be converted into the corresponding acid of formula (IV) by cautious hydrolysis with a dilute aqueous alcoholic solution of sodium hydroxide. In the particular case in which Z is a benzyl radical, the ester of formula (III) can be converted into the acid of formula (IV) by catalytic hydrogenation in the presence of palladium supported on carbon (Pd/C). The acid of formula (IV) is then condensed with a nitrogen compound of formula $HNR_6R_7$ in the presence of a coupling agent, for example DCC, in order to obtain compounds of general formula (I), in accordance with the following equation:

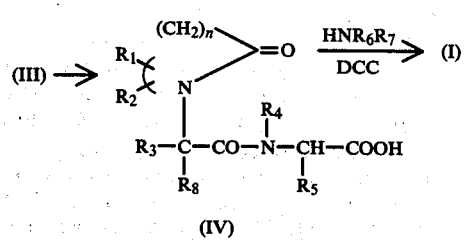

in which $R_1$ to $R_8$ and n have the same meanings as above.

In the reactions above, the coupling agents are those conventionally used in the formation of peptide bonds. Among these, use may be made of those mentioned in the article by Y. S. KLAUSNER and M. BODANSKY in Synthesis, 1972, 453–463, more particularly of dicyclohexylcarbodiimide and 1-ethoxy-carbonyl-2-ethoxy-1,2-dihydroquinoline.

The lactam-N-acetic acids of formula (II), which are starting materials, can be obtained, for example, by condensing a sodium salt of an $R_1$, $R_2$-substituted lactam of formula (VI) with a lower alkyl ester of an $R_3$,$R_8$-substituted chloro- or bromoacetic acid of formula (VII), the ester thus obtained of formula (VIII) then being hydrolyzed with a base such as sodium hydroxide to give the lactam-N-acetic acid of formula (II), in accordance with the following equation:

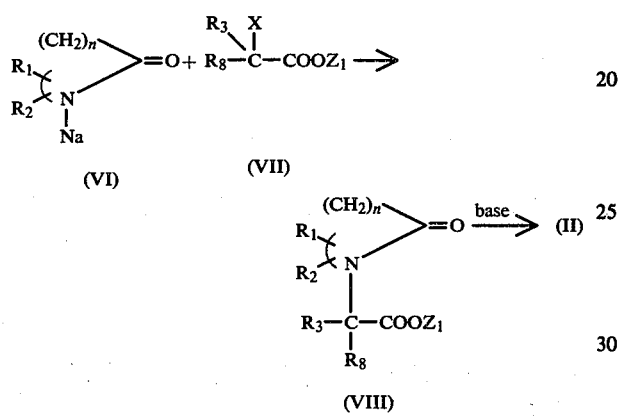

in which $R_1$, $R_2$, $R_3$, $R_8$ and n have the same meanings as above, $Z_1$ is an alkyl radical containing 1 to 4 carbon atoms or a benzyl radical and X is a chlorine or bromine atom.

The last-mentioned process has already been described in literature (see, for example, L. FONTANELLA et al., Pharm. Ed. Sci. 28,(1973),(6),448).

The following Examples are given for the purpose of illustrating the present invention:

1. Synthesis of esters of formula (III).

(a) N-(2-oxo-1-pyrrolidineacetyl)-glycine ethyl ester.

167.4 g (1.2 mole) of glycine ethyl ester hydrochloride are suspended in 4 liters of methylene chloride, the hydrochloric acid being neutralized by adding 168 ml (1.2 mole) of triethylamine. The reaction mixture is cooled to about 0° C. and a suspension of 171.6 g (1.2 mole) of 2-oxo-1-pyrrolidineacetic acid in 1500 ml methylene chloride is added. Without allowing the temperature to rise above 5° C., a solution of 272 g (1.4 mole) of DCC in 300 ml of methylene chloride is added dropwise to this mixture. Stirring is maintained for 2 hours at the same temperature and the reaction mixture is then allowed to return to ambient temperature, while stirring for 16 hours. 80 ml of acetic acid are then added, the reaction mixture is cooled to 0° C. and the precipitate is filtered off. The filtrate is evaporated to dryness and the residue redissolved in ethyl acetate, followed by filtering to remove insoluble matter. The filtrate is treated with highly absorbing active charcoal (Norite), again filtered and the filtrate is distilled at 190° C. at a pressure of 0.01 mm Hg. There are thus obtained 256 g of a syrup which is stirred with 1500 ml of anhydrous diethyl ether and which is crystallized by cooling in an ice bath. 177.5 g of N-(2-oxo-1-pyrrolidineacetyl)-glycine ethyl ester are thus obtained (yield: 64% of theory); M.P. 63°–64° C. The melting point of a sample recrystallized from a 1:2 v/v mixture of ethyl acetate and anhydrous diethyl ether is 64°–65° C.

Analysis: $C_{10}H_{16}N_2O_4$ (M.W. 228) calculated: C 52.63%; H 7.01%; N 12.28%; found: 52.70%; 6.98%; 12.20%.

IR spectrum (in KBr) in $cm^{-1}$: 3250 (NH amide); 1746 (CO ester); 1675 (CO lactam); 1655 (CO amide); 1540 (NH amide); 1192 (ester).

The following compounds of formula (III) are also prepared in the same manner. For these intermediate compounds, the IR spectrum is close to that indicated above. The melting point (or boiling point, as the case may be) and the yield are indicated for each compound:

(b) N-(2-Oxo-1-pyrrolidineacetyl)-glycine benzyl ester.

M.P. 92° C.; yield: 58% of theory. (Formula III: n=3; Z=benzyl).

(c) N-(alpha-Ethyl-5,5-dimethyl-2-oxo-1-pyrrolidineacetyl)-glycine ethyl ester.

M.P. 61° C.; yield: 68% of theory. (Formula III: n=3; $R_1$=$R_2$=5-methyl; $R_3$=Z=ethyl).

(d) N-(alpha,5,5-Trimethyl-2-oxo-pyrrolidineacetyl)-glycine ethyl ester.

M.P. 88° C.; yield: 55% of theory. (Formula III: n=3; $R_1$=$R_2$=5-methyl; $R_3$=methyl; Z=ethyl).

(e) N-(alpha-Ethyl-2-oxo-1-pyrrolidineacetyl)-glycine ethyl ester.

M.P. 70° C.; yield: 63% of theory. (Formula III: n=3; $R_3$=Z=ethyl).

(f) N-(alpha-Methyl-2-oxo-1-pyrrolidineacetyl)-glycine ethyl ester.

M.P. 48° C.; yield: 66% of theory. (Formula III: n=3; $R_3$=methyl; Z=ethyl).

(g) Ethyl 2-[1-(2-oxo-pyrrolidino)-cyclopropanecarboxamido]-acetate..

M.P. 171° C.; yield: 51% of theory. (Formula III: n=3; $R_3$+$R_8$=ethylene; Z=ethyl).

(h) N-(2-Oxo-1-pyrrolidineacetyl)-sarcosine ethyl ester.

B.P. 160° C./0.01 mm Hg; yield: 67% of theory. (Formula III: n=3; $R_4$=methyl; Z=ethyl).

(i) N-(2-Oxo-1-pyrrolidineacetyl)-sarcosine benzyl ester.

syrup; yield: 87% of theory; IR spectrum (film) in $cm^{-1}$: 1745, 1690, 1660, 1190, 742, 698 (Formula III: n=3; $R_4$=methyl; Z=benzyl).

(j) N-(2-Oxo-1-pyrrolidineacetyl)-alanine methyl ester.

syrup; yield: 79% of theory; IR spectrum (film) in $cm^{-1}$: 3280, 1745, 1690, 1665, 1540 (NH), 1215. (Formula III: n=3; $R_5$=Z=methyl).

(k) N-(2-Oxo-1-pyrrolidineacetyl)-2-phenylglycine ethyl ester.

M.P. 89° C.; yield: 80% of theory. (Formula III: n=3; $R_5$=phenyl; Z=ethyl).

(l) N-(2-Oxo-4-phenyl-1-pyrrolidineacetyl)-glycine ethyl ester.

M.P. 79° C.; yield: 77% of theory. (Formula III: n=3; $R_1$=4-phenyl; Z=ethyl).

(m) N-(2-Oxo-alpha-phenyl-1-pyrrolidineacetyl)-glycine ethyl ester.

M.P. 115° C.; yield: 66% of theory. (Formula III: n=3; $R_3$=phenyl; Z=ethyl).

(n) N-(5-Methyl-2-oxo-1-pyrrolidineacetyl)-glycine ethyl ester.

syrup; yield: 100% of theory; IR spectrum (in KBr) in $cm^{-1}$: 3300, 1740, 1680-1660, 1530, 1200.
(Formula III: n=3. $R_1$=5-methyl; Z=ethyl).

(o) N-(Hexahydro-2-oxo-1H-azepine-1-acetyl)-glycine ethyl ester.

M.P. 104° C.; yield 61% of theory. (Formula III: n=5; Z=ethyl).

(p) N-(alpha-n-Butyl-2-oxo-1-pyrrolidineacetyl)-glycine ethyl ester.

M.P. 79° C.; yield: 75% of theory. (Formula III: n=3; $R_3$=n-butyl; Z=ethyl).

(q) N-(3-n-Butyl-2-oxo-1-pyrrolidineacetyl)-glycine ethyl ester.

syrup; yield: 100% of theory; IR spectrum (film) in $cm^{-1}$: 3300, 2935 ($CH_2$), 1750, 1670, 1535, 1200. (Formula III: n=3; $R_1$=3-n-butyl; Z=ethyl).

2. Synthesis of acids of formula (IV).

(a) N-(2-Oxo-1-pyrrolidineacetyl)-glycine.

2.9 g (0.01 mole) of N-(2-oxo-1-pyrrolidineacetyl)-glycine benzyl ester (compound 1.b) above) are dissolved in 50 ml of acetic acid and hydrogenated in the presence of palladium supported on carbon (Pd/C) at ambient temperature, under a hydrogen pressure of 4 kg. The catalyst is filtered off, the filtrate is evaporated to dryness and the syrup obtained is triturated with anhydrous diethyl ether, a white powder being obtained: 2 g of N-(2-oxo-1-pyrrolidineacetyl)-glycine are thus isolated; M.P. 149°-150° C. Yield: 100% of theory.

Analysis: $C_8H_{12}N_2O_4$ (M.W. 200) calculated: C 48.0%; H 6.0%; N 14.0%, found: 47.6%; 6.21%; 13.88%.

IR spectrum (in KBr) in $cm^{-1}$: 3345 (NH), 1710 (CO), 1675 (CO), 1620 (CO), 1512 (NH), 1220 (C-OH).

N-(2-oxo-1-pyrrolidineacetyl)-sarcosine is prepared in the same manner; M.P. 178° C.; yield: 67% of theory. (Formula IV: n=3; $R_4$=methyl).

(b) 2-[1-(2-Oxo-pyrrolidino)-cyclopropanecarboxamido]-acetic acid.

(Formula IV: n=3; $R_3+R_8$=ethylene).

A solution of 3.5 g of sodium hydroxide in 80 ml of water is added to a solution of 20.4 g (0.08 mole) of ethyl 2-[1-(2-oxo-pyrrolidino)-cyclopropanecarboxamido]-acetate in 80 ml of methanol. The resulting solution is heated at 40° C. for 5 hours. The methanol is evaporated and the residue is taken up in water and acidified with concentrated hydrochloric acid to a pH of 1. The mixture is evaporated to dryness and the residue is recrystallized from water, 13 g of 2-[1-(2-oxo-pyrrolidino)-cyclopropanecarboxamido]-acetic acid being obtained (yield: 69% of theory); M.P. 211° C.

Analysis: $C_{10}N_{14}N_2O_4$ calculated: C 53.14%; H 6.24%; N 12.39%; found: 53.20%; 6.30%; 12.36%.

IR spectrum (in KBr) in $cm^{-1}$: 3460, 3300, 2700-2500, 1735 (CO), 1670 (CO), 1645 (CO), 1530 (NH), 1202.

3. Synthesis of lactams of general formula (I).

(a) 2-(2-Oxo-1-pyrrolidineacetamido)-acetamide (compound A). (Formula I: n=3; all R symbols are hydrogen).

17.1 g (0.075 mole) of N-(2-oxo-1-pyrrolidineacetyl)-glycine ethyl ester are dissolved in 350 ml of methanol. The solution is saturated with a current of ammonia (about 2 hours), stirring is maintained for 3 hours at ambient temperature. After the reaction mixture has been evaporated to dryness in vacuo, the residue crystallizes quickly, 14.9 g of 2-(2-oxo-1pyrrolidineacetamido)-acetamide being obtained (yield: 100% of theory); M.P. 147°-148° C.

Analysis: $C_8H_{13}N_3O_3$ (M.W. 199) calculated: C 48.24%; H 6.53%; N 21.10%; found: 48.11%; 6.49%; 21.24%.

IR spectrum (in KBr) in $cm^{-1}$: 3360 and 3320 ($NH_2$, NH), 1703 (CO-pyrrolidone), 1668 and 1652 (CO amide), 1565 (NH).

(b) N-n-Butyl-2-(2-oxo-1-pyrrolidineacetamido)-acetamide. (Compound B)

(Formula (I): n=3; $R_6$=n-butyl).

9.12 g (0.04 mole) of N-(2-oxo-1-pyrrolidineacetyl)-glycine ethyl ester are heated for 12 hours under reflux with 7.7 g (0.1 mole) of n-butylamine. The reaction mixture is evaporated to dryness and the crystallized residue is washed with diethyl ether. The residual product is dried after filtration and washing with diethyl ether. 9.9 g of N-n-butyl-2-(2-oxo-1-pyrrolidineacetamido)-acetamide are thus obtained (yield: 97% of theory); M.P. 105°-106° C.

Analysis: $C_{12}H_{21}N_3O_3$ (M.W. 255) calculated: C 56.51%; H 8.23%; N 16.47%; found: 56.66%; 8.34%; 16.36%.

IR spectrum (in KBr) in $cm^{-1}$: 3285 (NH), 1680 (CO lactam), 1670 and 1650 (CO amide), 1550 (NH).

(c) N-Methyl-2-(2-oxo-1-pyrrolidineacetamido)-acetamide. (Compound C) (Formula (I): n=3; $R_6$=methyl).

31 g (1 mole) of methylamine are added to 18.24 g (0.08 mole) of N-(2-oxo-1-pyrrolidineacetyl)-glycine ethyl ester and the reaction mixture is kept at −20° C. for 8 hours, while stirring. It is then evaporated and the residue is recrystallized from absolute ethanol, 15.7 g. of N-methyl-2-(2-oxo-1-pyrrolidineacetamido)-acetamide being obtained (yield: 92% of theory); M.P. 139°-140° C.

Analysis: $C_9H_{15}N_3O_3$ (M.W. 213) calculated: C 50.74%; H 7.04%; N 19.72%; found: 50.80%; 7.10%; 19.60. IR spectrum (in KBr) in $cm^{-1}$: 3250 (NH), 1680 and 1660 (CO), 1550 (NH).

(d)
2-(2-Oxo-1-pyrrolidineacetamido)-N-phenylacetamide (Compound D). (Formula (I): n=3; $R_6$=phenyl).

23.2 g (0.102 mole) of N-(2-oxo-1-pyrrolidineacetyl)-glycine ethyl ester are mixed in a round-bottomed flask with 51 ml (0.51 mole) of aniline and 10.5 ml of methanol. 0.39 g (0.017 mole) of sodium is added portionwise to this solution. The temperature of the reaction mixture is brought to about 50° C. in order to dissolve the sodium completely and reflux is then maintained for about 17 hours. The methanol is then removed and 150 ml of anhydrous toluene are added. The precipitate formed is filtered off, washed with diethyl ether and recrystallized from absolute ethanol, 7.4 g 2-(2-oxo-1-pyrrolidineacetamido)-N-phenylacetamide being obtained (yield: 26.5% of theory); M.P. 200°–201° C.

Analysis: $C_{14}H_{17}N_3O_3$ calculated: C 61.14%; H 6.18%; N 15.28%; found: 61.12% 6.22%; 15.30%.

IR spectrum (in KBr) in cm$^{-1}$: 3320 (NH), 1690, 1670 and 1653 (CO), 1555 (NH), 750 and 692 (phenyl).

(e)
2-(N-Methyl-2-oxo-1-pyrrolidineacetamido)-N-phenylacetamide. (Compound E)

(Formula (I): n=3; $R_4$=methyl; $R_6$=phenyl).

A solution of 3.8 g (0.04 mole) of aniline in 40 ml methylene chloride is added to a suspension of 8.6 g (0.04 mole) of N-(2-oxo-1-pyrrolidineacetyl)-sarcosine in 60 ml of methylene chloride. The reaction mixture is cooled to 0° C. and 9.2 g (0.044 mole) of DCC, dissolved in 20 ml of methylene chloride, are added dropwise. Stirring is maintained for 2 hours at a temperature between 0° and 5° C. and then for 18 hours at ambient temperature. The dicyclohexylurea formed is then filtered and 6 ml of acetic acid are added to the filtrate, which is evaporated to dryness in vacuo. The residue is taken up in ethyl acetate, insoluble matter (dicyclohexylurea) is filtered off and the filtrate is evaporated to dryness. A syrup is obtained which is stirred with toluene in order to crystallize it. Silica column chromatography can also be used (eluent: methanol/chloroform (1:9 v/v)). The product is filtered off, washed with diethyl ether and dried, 9.5 g of 2-(N-methyl-2-oxo-1-pyrrolidineacetamido)-N-phenylacetamide thus being obtained (yield: 82% of theory); M.P. 145°–146° C.

Analysis: $C_{15}H_{19}N_3O_3$ (M.W. 289) calculated: C 62.33%; H 6.57%; N 14.54% found: 62.30%; 6.50%; 14.48%.

IR spectrum (in KBr) in cm$^{-1}$: 3320 and 3300 (NH), 1680, 1655 and 1610 (CO), 1550 (NH), 757 and 692 (phenyl).

The following compounds of general formula (I) are also prepared in the manner described above:

Compound F
N-isopropyl-2-(2-oxo-1-pyrrolidineacetamido)-acetamide

M.P. 140° C.; yield: 80% of theory. (Formula I: n=3; $R_6$=isopropyl).

Compound G
2-(alpha-ethyl-5,5-dimethyl-2-oxo-1-pyrrolidineacetamido)-acetamide.

M.P. 151° C.; yield: 95% of theory. (Formula I: n=3; $R_1$=$R_2$=5-methyl; $R_3$=ethyl).

Compound H
2-(alpha,5,5-trimethyl-2-oxo-1-pyrrolidineacetamido)-acetamide.

M.P. 202° C.; yield: 80% of theory. (Formula I: n=3; $R_1$=$R_2$=5-methyl; $R_3$=methyl).

Compound I
2-(alpha-ethyl-5,5-dimethyl-2-oxo-1-pyrrolidineacetamido)-N-propylacetamide.

M.P. 177° C.; yield: 90% of theory. (Formula I: n=3; $R_1$=$R_2$=5-methyl; $R_3$=ethyl; $R_6$=propyl).

Compound J
2-(alpha-methyl-2-oxo-1-pyrrolidineacetamido)-acetamide.

M.P. 119° C.; yield: 85% of theory. (Formula I: n=3; $R_3$=methyl).

Compound K
2-(alpha-ethyl-2-oxo-1-pyrrolidineacetamido)-acetamide.

M.P. 122° C.; yield: 70% of theory. (Formula I: n=3; $R_3$=ethyl).

Compound L
2-[1-(2-oxo-pyrrolidino)-cyclopropanecarboxamido]-acetamide.

M.P. 180° C.; yield: 78% of theory. (Formula I: n=3; $R_3$+$R_8$=ethylene).

Compound M
N,N-ddimethyl-2-(2-oxo-1-pyrrolidineacetamido)-acetamide.

M.P. 121° C.; yield: 40% of theory. (Formula I: n=3; $R_6$=$R_7$=methyl).

Compound N
2-(N-methyl-2-oxo-1-pyrrolidineacetamido)-acetamide.

M.P. 159° C.; yield: 40% of theory. (Formula I: n=3; $R_4$=methyl).

Compound O
N-methyl-2-(N-methyl-2-oxo-1-pyrrolidineacetamido)-acetamide.

M.P. 111° C.; yield: 61% of theory. (Formula I: n=3; $R_4$=$R_6$=methyl).

Compound P
N,N-dimethyl-2-(N-methyl-2-oxo-1-pyrrolidineacetamido)-acetamide. M.P. 78° C.; yield: 10% of theory. (Formula I: n=3; $R_4$=$R_6$=$R_7$=methyl).

Compound Q
2-methyl-2-(2-oxo-1-pyrrolidineacetamido)-acetamide.

M.P. 173° C.; yield: 50% of theory. (Formula I: n=3; $R_5$=methyl).

Compound R
2-(2-oxo-1-pyrrolidineacetamido)-2-phenylacetamide.

M.P. 195° C.; yield: 53% of theory. (Formula I: n=3; $R_5$=phenyl).

Compound S 2-(2-oxo-4-phenyl-1-pyrrolidineacetamido)-acetamide.

M.P. 160° C.; yield: 90% of theory. (Formula I: n=3; R$_1$=4-phenyl).

Compound T 2-(5-methyl-2-oxo-1-pyrrolidineacetamido)-acetamide.

M.P. 131° C.; yield: 33% of theory. (Formula I: n=3; R$_1$=5-methyl).

Compound U 2-(2-oxo-alpha-phenyl-1-pyrrolidineacetamido)-acetamide.

M.P. 174° C.; yield: 85% of theory. (Formula I: n=3; R$_3$=phenyl).

Compound V 2-(hexahydro-2-oxo-1H-azepine-1-acetamido)-acetamide.

M.P. 128° C.; yield: 80% of theory. (Formula I: n=5).

Compound W 2-(alpha-n-butyl-2-oxo-1-pyrrolidineacetamido)-acetamide.

M.P. 93° C.; yield: 70% of theory. (Formula I: n=3; R$_3$=n-butyl).

Compound X 2-(3-n-butyl-2-oxo-1-pyrrolidineacetamido)-acetamide.

M.P. 152° C.; yield: 75% of theory. (Formula I: n=3; R$_1$=3-n-butyl).

Compound Y

N-tert-butyl-2-(2-oxo-1-pyrrolidineacetamido)-acetamide.

M.P. 149°-150° C.; yield: 25% of theory. (Formula I: n=3; R$_6$=tert-butyl).

Pharmacological results

Certain of the compounds prepared above have been tested pharmacologically, the results obtained being given below.

I. Action on mnemic processes:

(A) The action on mnemic processes is first shown by the ability of the compounds to improve a type of memory retention in rats. The principle of the active avoidance test (see M. GREINDL and S. PREAT, Arch. Int. Pharmacodyn. Therap. 223,(1976),(1),168–171) developed in our laboratories and used for this purpose may be described as follows: the reaction of withdrawal of a rat's paw when subjected to an increasing and measured pressure is observed. The pressure at which the withdrawal reaction takes place is called the reaction threshold. This threshold is expressed by the number of graduations of the scale of the apparatus used (Analgesy meter UGO BASILE - Milano) and thus corresponds to the minimum pressure which brings about withdrawal when applied to the animal's paw. It is read directly from the scale of the apparatus used.

When tested 24 hours later, the control animals show no apparent retention of the previous test: avoidance takes place at a stimulation intensity comparable to that applied the day before. Inversely, animals treated with a substance having a positive effect on the mnemic processes (for example, piracetam) show a significant degree of retention: the stimulus at which the rats react by a reflex of avoidance is statistically lower than that of the control animals. A minimum of 20 rats are used per test (10 treated rats and 10 control rats) and the active dose is defined as the minimum dose which reduces the stimulus to below 11 graduations.

Subcutaneous administration of compounds of general formula (I), namely compounds A, G, H, I, J, K, L, N, O, P, Q, R, V, W, give, under these conditions, the effects indicated in Table I below. This Table I shows that, in this test, these compounds all exhibit an activity which is superior to that of piracetam, the action of which on mnemic processes is well known:

TABLE I

| compound | Active dose mg/kg | Active dose mM/kg |
|---|---|---|
| A | 0.40 | 0.002 |
| G | 0.51 | 0.002 |
| H | 0.0024 | 0.00001 |
| I | 5.94 | 0.02 |
| J | 0.21 | 0.001 |
| K | 4.54 | 0.02 |
| L | 0.23 | 0.001 |
| N | 2.13 | 0.01 |
| O | 2.27 | 0.01 |
| P | 2.41 | 0.01 |
| Q | 2.13 | 0.01 |
| R | 2.75 | 0.01 |
| V | 2.27 | 0.01 |
| W | 2.55 | 0.01 |
| Piracetam | 3.50 | 0.025 |

(B) The action on mnemic processes is also shown by the reduction of the spinal fixation time, a test which has been described in literature (see C. GIURGEA & F. MOURAVIEFF-LESUISSE, Arch. Int. Pharmacodyn. 191/2,(1971), 279) as an elementary memory model and which provides pharmacological reactivity in good correlation with clinical physiopathology. In the rat, after unilateral section of the cerebellum, there is a postural asymmetry of the hind paws. This asymmetry may persist, even after spinal section, if the animal has passed a sufficient period of time in this position. This time, which is called the spinal fixation time, is 45 minutes under the experimental conditions applied here.

On the other hand, if spinal section is performed before the expiry of this period of time, for example 35 minutes after the onset of the asymmetry, the latter disappears.

No animal treated with placebos retains the asymmetry under these conditions.

Inversely, any product which allows the rats to retain the asymmetry (thus effecting spinal fixation) when the spinal section is performed after 35 minutes, is considered to be active.

Intraperitoneal administration of compound A gives rise to the effects described in Table II. By "number of animals" is to be understood the number of animals which responded positively to the test, in relation to the number of animals tested at the indicated dose:

TABLE II

| compound | Active dose mg/kg | Active dose mM/kg | Number of animals |
|---|---|---|---|
| A | 6.4 | 0.032 | 3/7 |
|   | 20.0 | 0.1 | 4/5 |

TABLE II-continued

| compound | Active dose mg/kg | Active dose mM/kg | Number of animals |
|---|---|---|---|
| Piracetam | 30 | 0.2 | 4/9* |

*Giurgea et al., loc.cit.

II. Protection against aggressions of the hypoxic type.

Protection against aggressions of the hypoxic type is shown by a reduction of the lethality induced by a curarizer, the duration of action of which is short, namely oxydipentonium chloride (Brevatonal). At the doses used, this curarizer brings about a respiratory depression which, in turn, brings about a hypoxi-hypercapnic syndrome. A compound capable of protecting the brain during this brief period of hypoxia ensures survival. The compounds are administered to groups of 10 mice one hour before the injection of the curarizer; in a parallel test, a control group of 10 mice are given physiological salt solution before the curarizer. This test has also been developed in our laboratories (see, for the principle of this test, S. LEVIS et al.; Arch. Int. Pharmacodyn. Therap. 93,(1953),1,46–54).

Intraperitoneal administration of compounds of general formula (I), namely, products A, B, F, G, H, I, J, K, L, gives the results shown in Table III:

TABLE III

| Product | Dose mg/kg | Dose mM/kg | Proportion of survivors Animals treated | Control animals |
|---|---|---|---|---|
| A | 64 | (0.32) | 7/10 | 1/10 |
| B | 2.6 | (0.01) | 6/10 | 1/10 |
|   | 8.2 | (0.032) | 8/10 | 1/10 |
| F | 24 | (0.1) | 4/10 | 0/10 |
| G | 2.6 | (0.01) | 4/10 | 1/10 |
|   | 25.5 | (0.1) | 6/10 | 1/10 |
| H | 2.4 | (0.01) | 6/10 | 2/10 |
|   | 24 | (0.1) | 10/10 | 1/10 |
| I | 30 | (0.1) | 5/10 | 1/10 |
|   | 95 | (0.32) | 8/10 | 1/10 |
| J | 21 | (0.1) | 6/10 | 1/10 |
|   | 68 | (0.32) | 10/10 | 1/10 |
| K | 23 | (0.1) | 7/10 | 1/10 |
| L | 23 | (0.1) | 8/10 | 1/10 |
| Piracetam | 45 | (0.32) | 1/10 | 0/10 |
|   | 142 | (1.0) | 4/10 | 2/10 |
|   | 454 | (3.2) | 8/10 | 1/10 |

Therefore, the compounds tested possess, for an equal dose, a far greater activity than piracetam.

III. Cardiac activity.

We have also observed that the compounds of general formula (I) possess a significant cardiac activity. This has been shown by the method employing the papillary muscle isolated from the rabbit heart, according to the method of H. G. Schoepke and F. E. Shiddeman, J. Pharmacol. Exptl. Therap. 133,(1961), 171.

The reactivity of various compounds of general formula (I) after each experiment is checked against theophylline. Table IV gives some of the results observed, expressed as a percentage increase of the tension measured.

TABLE IV

| Compound | Dose (μg/ml) | Results (%) |
|---|---|---|
| E | 100 | 22 |
| H | 10 | 10 |
| K | 100 | 44 |
| M | 10 | 10 |

TABLE IV-continued

| Compound | Dose (μg/ml) | Results (%) |
|---|---|---|
| X | 100 | 25 |
| Theophylline | 100 | 38 |

In addition, product H showed, in the same test, a protective action against anoxia.

IV. Toxicity.

The tested compounds have a remarkably low toxicity. Table V gives the toxicities, after intravenous administration, of some of the compounds of the present invention:

TABLE V

| Product | LD$_{50}$ mM/kg rat | mg/kg |
|---|---|---|
| A | >5 | >1000 |
| B | >4 | >1020 |
| F | >3 | > 723 |
| J | >2.6 | > 554 |
| K | >2.5 | > 568 |
| H | >3.1 | > 747 |
| G | >2.8 | > 714 |
| I | >2.5* | > 743 |

*intraperitoneal administration.

V. Posology and administration

The compounds of general formula (I) can be administered per os in the form of solid or liquid compositions containing conventional excipients, for example, in the form of tablets, pills, sugar-coated pills, gelatine capsules, solutions, syrup or the like, or in the form of suppositories for rectal administration or in the form of injectable solutions or suspensions. Compositions for parenteral administration include the known forms of this type of administration, for example, aqueous and oily solutions, suspensions or emulsions.

The posology is between 20 and 2000 mg of compound per day, obviously with variations depending upon the weight and condition of the subject to be treated and also depending upon the mode of administration.

By way of example, a tablet composition containing a compound of general formula (I) is as follows:

| compound A | 400 mg |
|---|---|
| Starch | 61 mg |
| Polyvinyl-pyrrolidone | 8 mg |
| Talc | 26 mg |
| Magnesium stearate | 5 mg |

We claim:

1. An N-substituted 2-pyrrolidinone having the formula $$R_3-\underset{\underset{R_8}{|}}{\overset{\overset{R_1}{|}}{C}}-CO-N-\underset{\underset{R_4}{|}}{\overset{\overset{R_5}{|}}{CH}}-CO-N\overset{R_6}{\underset{R_7}{}}$$

wherein $R_1$, $R_2$, $R_3$, $R_4$, $R_5$, $R_6$ and $R_7$ represent independently a hydrogen atom, alkyl having 1 to 4 carbon atoms or phenyl, and R₈ is a hydrogen atom or R₈ and R₃ together are ethylene or trimethylene.

2. A compound as claimed in claim 1, namely 2-(2-oxo-1-pyrrolidineacetamido)-acetamide.

3. A compound as claimed in claim 1, namely N-n-butyl-2-(2-oxo-1-pyrrolidineacetamido)-acetamide.

4. A compound as claimed in claim 1, namely N-isopropyl-2-(2-oxo-1-pyrrolidineacetamido)-acetamide.

5. A compound as claimed in claim 1, namely 2-(alpha-ethyl-5,5-dimethyl-2-oxo-1-pyrrolidineacetamido)-acetamide.

6. A compound as claimed in claim 1, namely 2-(alpha,5,5-trimethyl-2-oxo-1-pyrrolidineacetamido)-acetamide.

7. A compound as claimed in claim 1, namely 2-(alpha-ethyl-5,5-dimethyl-2-oxo-1-pyrrolidineacetamido)-N-n-propylacetamide.

8. A compound as claimed in claim 1, namely 2-(alpha-methyl-2-oxo-1-pyrrolidineacetamido)-acetamide.

9. A compound as claimed in claim 1, namely 2-(alpha-ethyl-2-oxo-1-pyrrolidineacetamido)-acetamide.

10. A compound as claimed in claim 1, namely 2-[1-(2-oxo-pyrrolidino)cyclopropanecarboxamido]-acetamide.

11. A compound as claimed in claim 1, namely 2-(N-methyl-2-oxo-1-pyrrolidineacetamido)-acetamide.

12. A composition having activity on the mnemic processes, a protective activity against aggressions of the hypoxic type and which is useful in the prevention and treatment of cerebrovascular or cardiovascular injuries comprising an effective amount for said uses of an N-substituted 2-pyrrolidinone having the formula

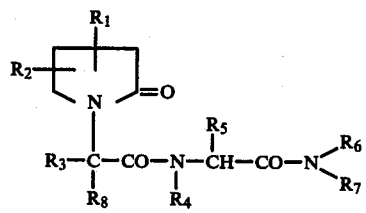

wherein $R_1$, $R_2$, $R_3$, $R_4$, $R_5$, $R_6$ and $R_7$ represent independently a hydrogen atom, alkyl having 1 to 4 carbon atoms or phenyl, and R is a hydrogen atom or $R_8$ and $R_3$ together are ethylene or trimethylene, and a pharmaceutically acceptable solid or liquid carrier.

* * * * *